(12) United States Patent
Jarhede et al.

(10) Patent No.: US 8,093,005 B2
(45) Date of Patent: Jan. 10, 2012

(54) PREPARATION AND USE OF A REACTIVE SOLID SUPPORT SURFACE

(75) Inventors: Tanja Jarhede, Uppsala (SE); Per Kjellin, Uppsala (SE); Anita Larsson, Uppsala (SE); Hans Sjobom, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 12/581,431

(22) Filed: Oct. 19, 2009

(65) Prior Publication Data

US 2010/0041127 A1 Feb. 18, 2010

Related U.S. Application Data

(62) Division of application No. 11/249,038, filed on Oct. 11, 2005, now abandoned.

(60) Provisional application No. 60/618,655, filed on Oct. 13, 2004.

(30) Foreign Application Priority Data

Oct. 13, 2004 (SE) ....................................... 0402476

(51) Int. Cl.
*G01N 33/53* (2006.01)
*G01N 31/00* (2006.01)

(52) U.S. Cl. .......... 435/7.1; 435/4; 435/287.9; 436/501; 436/518; 436/525; 436/529; 436/535; 436/809; 427/287; 427/337; 427/338; 422/57

(58) Field of Classification Search ......................... None
See application file for complete search history.

(56) References Cited

U.S. PATENT DOCUMENTS

| | | | |
|---|---|---|---|
| 5,242,828 A | 9/1993 | Bergstrom et al. | |
| 5,313,264 A | 5/1994 | Ivarsson et al. | |
| 5,436,161 A * | 7/1995 | Bergstrom et al. | 422/425 |
| 5,492,840 A | 2/1996 | Malmqvist et al. | |
| 6,475,808 B1 | 11/2002 | Wagner et al. | |
| 6,800,296 B1 * | 10/2004 | Langer et al. | 424/484 |
| 6,897,073 B2 * | 5/2005 | Wagner et al. | 436/518 |
| 2003/0040027 A1 | 2/2003 | Ritter et al. | |
| 2003/0068446 A1 | 4/2003 | Mirkin et al. | |
| 2004/0115721 A1 | 6/2004 | Mao et al. | |
| 2006/0040274 A1 | 2/2006 | Tsinberg | |
| 2006/0040377 A1 | 2/2006 | Tsinberg | |

FOREIGN PATENT DOCUMENTS

| | | |
|---|---|---|
| WO | WO 92/21769 | 12/1992 |
| WO | WO 03/005890 | 1/2003 |
| WO | WO 2004/005477 | 1/2004 |

OTHER PUBLICATIONS

Johnsson et al. ("Immobilization of Proteins to a Carboxymethyldextran-Modified Gold Surface for Biospecific Interaction Analysis in Surface Plasmon Resonance Sensors," Anal. Biochem. vol. 198 (1991) 268-277).*
"SPR-based Assays for Plasma Samples—Strategies to Improve Plasma Measurements", presented as Poster No. P08043 at the Society for Biochemical Screening Conference, Portland, OR, Sep. 22-25, 2003.
Biacore, Sensor Surface Handbook, Oct. 2003 ed., "Problems with Non-specific Binding", p. 84-86.
Chapman, R., et al., "Polymeric Thin Films that Resist the Adsorption of Proteins and the Adhesion of Bacteria", Langmuir, 17:1225-1233, 2001.
Chapman, R., et al., "Surveying for Surfaces that Resist the Adsorption of Proteins", Journal of the American Chemical Society, 122:8303-8304, 2000.
Johnson, B., et al., "Immobilization of Proteins to a Carboxymethyldextran-Modified Gold Surface for Biospecific Interaction Analysis in Surface Plasmon Resonance Sensors", Analytical Biochemistry, 198:268-277, 1991.
Siegers, C., et al., "Self-assembled Monolayers of Dendritic Polyglycerol Derivatives on Gold that Resist the Adsorption of Proteins", Chemistry, 10(11):2831-2838, 2004.
Frederix, F., et al., "Reduced Nonspecific Adsorption on Covalently Immobilized Protein Surfaces Using Poly (ethylene oxide) Containing Blocking Agents", J Biochem Biophys Methods, 58(1):67-74, 2004.

* cited by examiner

*Primary Examiner* — Lisa Cook

(57) ABSTRACT

A method of preparing a protein-resistant reactive solid support surface is disclosed. The method comprises the steps of providing a solid support having a hydrogel coating with a plurality of binding elements, coupling a protein resistant compound to the hydrogel via a first fraction of the binding elements, and coupling at least one binding agent to the hydrogel via a second fraction of the binding elements, whereby the protein resistant compound and the at least one binding agent are co-immobilized to the hydrogel. Also the use of the reactive surface in analysis, such as immunogenicity assays, is disclosed.

20 Claims, 2 Drawing Sheets

PREPARATION AND USE OF A REACTIVE SOLID SUPPORT SURFACE

CROSS-REFERENCE TO RELATED APPLICATION

This application is a divisional of U.S. patent application Ser. No. 11/249,038 filed Oct. 11, 2005, now abandoned, which claims the benefit under 35 U.S.C. §119(e) of U.S. Provisional Patent Application No. 60/618,655 filed Oct. 13, 2004; and also claims priority to Swedish Application No. 0402476-6 filed Oct. 13, 2004; both of these applications are incorporated herein by reference in their entireties.

BACKGROUND OF THE INVENTION

1. Field of the Invention

The present invention relates to a method for preparing a solid support surface having binding agents, such as analyte-specific ligands, immobilized thereto, and more particularly to such a surface which resists non-specific binding. The invention also relates to the use of the prepared solid support surface in analysis, such as immunogenicity assays, and to a protein-resistant solid support surface for coupling of binding agents thereto.

2. Description of the Related Art

A variety of analytical techniques are used to characterize interactions between molecules, particularly in the context of assays directed to the detection and interaction of biomolecules. For example, antibody-antigen interactions are of fundamental importance in many fields, including biology, immunology and pharmacology. In this context, many analytical techniques involve binding of a "ligand", such as an antibody, to a solid support, followed by contacting the ligand with an "analyte", such as an antigen. Following contact of the ligand and analyte, some characteristic is measured which is indicative of the interaction, such as the ability of the ligand to bind the analyte. It is often desired that after measurement of the interaction, it should be possible to dissociate the ligand-analyte pair in order to "regenerate" free ligand, thereby enabling reuse of the ligand surface for a further analytical measurement.

Analytical sensor systems that can monitor such molecular interactions in real time are gaining increasing interest. These systems are often based on optical biosensors and usually referred to as interaction analysis sensors or biospecific interaction analysis sensors. A representative such biosensor system is the BIACORE® instrumentation sold by Biacore AB (Uppsala, Sweden), which uses surface plasmon resonance (SPR) for detecting interactions between molecules in a sample and molecular structures immobilized on a sensing surface. With the BIACORE® systems it is possible to determine in real time without the use of labeling not only the presence and concentration of a particular molecule in a sample, but also additional interaction parameters such as, for instance, the association rate and dissociation rate constants for the molecular interaction.

Since the SPR-based detection, like several other so-called label-free detection techniques, senses mass changes at the sensor surface, non-specific binding to the sensor surface will also be sensed, giving a false addition to the detected response at the surface. This is particularly the case where the samples are complex mixtures such as a blood serum or crude cell extract. The non-specific binding may arise from binding of non-analyte molecules in the sample to the immobilized ligand or from non-specific binding of analyte or non-analyte molecules to the actual sensor surface. In, for example, immunogenicity studies where antibodies in serum samples are analyzed, problems in most cases arise due to non-specific binding from non-analyte species in the serum, this non-specific binding often being greater than the specific binding of the target antibody.

It is known that poly(ethylene glycol) (PEG) coatings may significantly reduce the non-specific adsorption of proteins and cells to a surface.

U.S. Pat. No. 6,475,808 discloses an assay device comprising a substrate with a surface having an array of discrete array-regions. An ordered hydrophobic monolayer of alkyl chains is chemisorbed or physisorbed to the surface, and a hydrophilic monolayer formed from poly(ethylene glycol) chains is covalently linked to the hydrophobic monolayer. A plurality of protein-immobilizing groups are covalently attached to a selected fraction of the poly(ethylene glycol) chains within the array regions. The hydrophobic monolayer and the poly(ethylene glycol) chains are effective in combination to resist non-specific protein binding.

WO 2004/005477 discloses a microarray which comprises a substrate having a substantially planar surface comprising an organic-chemically modified dielectric-coated reflective metal, e.g., gold, and a plurality of proteins stably attached to the surface via a chemical adapter, e.g., a functionalized dextran. After spotting the proteins onto the substrate surface, the surface may be derivatized with poly(ethylene glycol) or a poly(ethylene glycol) analogue to inhibit non-specific protein adsorption.

WO 03/005890 discloses an optical fiber surface plasmon resonance (SPR) sensor having a gold surface to which a dextran layer is bound via a self-assembled monolayer (SAM) of 11-mercapto-dodecanol. Anti-myoglobin antibodies are attached to the dextran via carboxylated hydroxyl groups thereof. To eliminate non-specific binding to the sensor, thiol-terminated poly(ethylene glycol), e.g., methoxy-PEG-thiol, may be coupled to the gold surface through a gold-thiol bond or to the dextran. Immobilized PEG surrounding the sensor will prevent non-specific interactions with the surface while allowing specific receptor-ligand interactions.

The present invention seeks to provide an improved method for preparing a protein-resistant solid support surface having binding agents immobilized thereon.

BRIEF SUMMARY OF THE INVENTION

The above and other objects and advantages are provided by a method for preparing a solid support surface with immobilized binding agent(s) and a protein resistant compound, which method basically is characterized in that the solid support surface has a hydrogel coating, and that (i) a protein resistant compound, such as, e.g., poly(ethylene glycol) or a derivative thereof, and (ii) a binding agent(s) are coupled to the hydrogel to be co-immobilized thereon. In this way, it is possible to provide a solid support surface, such as a sensing surface, which has a high level of binding agent, e.g., analyte-specific ligand, simultaneously with a sufficient level of a protein resistant compound to effectively resist non-specific binding.

In one aspect, the present invention therefore provides a method of preparing a reactive solid support surface, which method comprises the steps of:

a) providing a solid support having a hydrogel coating with a plurality of binding elements, b) coupling a protein resistant compound to the hydrogel via a first fraction of the binding elements, and c) coupling at least one binding agent to the hydrogel via a second fraction of the binding elements, whereby the protein resistant compound and the at least one binding agent are co-immobilized to the hydrogel.

In another aspect, the present invention provides the use of a reactive solid support surface prepared according to the method aspect above for analysis of an analyte in a sample.

In one embodiment of this aspect, the analysis comprises immunogenicity studies.

In still another aspect, the present invention provides a protein resistant solid support surface for coupling of binding agents, comprising a hydrogel layer with a plurality of binding elements, wherein a selected fraction of the binding elements are coupled to a protein resistant compound, and the remaining binding elements are free for coupling of one or more binding agents to the surface.

DEFINITIONS

Figure 1:
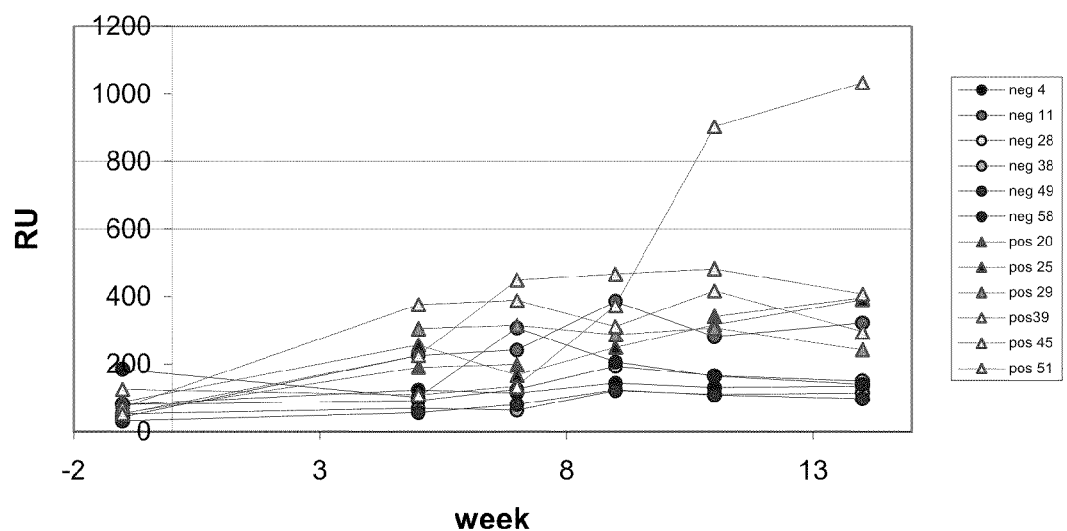
FIG. 1 is a diagram showing rat serum anti-IgE responses versus time after immunization for vaccinated and control animals, respectively, on a sensor surface with immobilized IgE.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

The term "hydrogel" is used herein in the sense defined by Merrill, E. W. et al. (1986), *Hydrogels in Medicine and Pharmacy*, Vol. III, Ed. Peppas, N. A., Chapter 1, CRC Press (the disclosure of which is incorporated by reference herein). As stated therein "a 'hydrogel' presents a surface layer of bound molecules which by reason of their chemical nature hold a large fraction of water, in which the molecules are predominantly in an amorphous, water-solvated state."

"Array" as used herein generally relates to a linear or two-dimensional array of discrete regions, each having a finite area, formed on a continuous surface of a solid support and supporting one or more binding agents.

"Solid support" as used herein is meant to comprise any solid (flexible or rigid) substrate onto which it is desired to apply one or more binding agents, optionally in the form of an array. The substrate surface supporting the binding agents may be the surface of a layer of material different from that of the rest of the substrate.

"Activation" as used herein means a modification of a functional group on a molecule to enable coupling to another molecule.

"Binding agent" as used herein means a species that exhibits a (usually specific) binding activity towards a target molecule. The binding agent may be a member of a specific binding pair, including, for instance, polypeptides, such as proteins or fragments thereof; nucleic acids, e.g., oligonucleotides, polynucleotides, and the like. The binding agent is often a ligand or a capture agent.

"Target molecule" as used herein refers to a molecule, present in a medium, which is the object of attempted capture.

"Specific binding pair" (abbreviated "sbp") as used herein describes a pair of molecules (each being a member of a specific binding pair) that are naturally derived or synthetically produced. One of the pair of molecules has a structure (such as an area or cavity) on its surface that specifically binds to (and is therefore defined as complementary with) a particular structure (such as a spatial and polar organisation) of the other molecule, so that the molecules of the pair have the property of binding specifically to each other. Examples of types of specific binding pairs (without any limitation thereto) are antigen-antibody, antibody-hapten, biotin-avidin, ligand-receptor (e.g., hormone receptor, peptide-receptor, enzyme-receptor), carbohydrate-protein, carbohydrate-lipid, lectin-carbohydrate, nucleic acid-nucleic acid (such as oligonucleotide-oligonucleotide).

"Capture agent" refers to a species that can be immobilized to a solid support surface and which can bind to another species, such as a ligand or a second capture agent.

"Ligand" as used herein means a molecule that has a known or unknown affinity for a given analyte. The ligand may be a naturally occurring molecule or one that has been synthesized.

"Analyte" as used herein is a molecule, e.g., a macromolecule, such as a polynucleotide or polypeptide, the presence, amount, identity and/or interaction kinetics of which are to be determined. The analyte may also be a small molecule. The analyte is recognized by a particular ligand forming an analyte/ligand complex.

"Antibody" refers to an immunoglobulin which may be natural or partly or wholly synthetically produced and also includes active fragments, including Fab antigen-binding fragments, univalent fragments and bivalent fragments. The term also covers any protein having a binding domain that is homologous to an immunoglobulin binding domain. Such proteins can be derived from natural sources, or partly or wholly synthetically produced. Exemplary antibodies are the immunoglobulin isotypes and the Fab, Fab', F(ab')$_2$, scFv, Fv, dAb, and Fd fragments.

"Sensing surface" as used herein is to be interpreted in a broad sense and means any surface to which a ligand is or can be immobilized for detecting an analyte/ligand interaction.

"Surface sensitive detection technique" refers to a detection technique where a change in a property of a sensing surface is measured as being indicative of binding interaction at the sensing surface. Examples of surface sensitive detection techniques are given in the detailed description of the invention below.

DETAILED DESCRIPTION OF THE INVENTION

As mentioned above, the present invention relates to the preparation of a solid support surface, such as a sensing surface, which has immobilized on the surface (i) a binding agent(s) and (ii) a protein resistant compound, which surface permits specific binding of, e.g., analyte to the immobilized binding agents while resisting or preventing binding of non-specifically binding species to the surface.

According to the invention, this is achieved by providing a substrate surface having a hydrogel layer attached thereto, and coupling the protein resistant compound and the one or more binding agents to the hydrogel, such that the protein resistant compound and the binding agents are co-immobilized to the hydrogel i.e., that the two molecular species are intermixed laterally on the hydrogel. While the coupling of protein resistant compound and binding agent(s) preferably is performed sequentially in the above order, it may optionally be effected in the opposite order, i.e., first coupling binding agent(s) and then protein resistant compound, or, possibly, also simultaneously.

The "protein resistant compound" is basically a biocompatible organic compound which, after coupling to the hydrogel, lacks (especially polar) functional or charged groups that may interact with the protein, or groups that may interact via hydrophobic interaction. It usually incorporates a hydrogen bond accepting group or groups, and mostly lacks hydrogen bond donors. The compound is often a hydrophilic polymer, especially a polymer having hydrogel-like properties. At least when the protein resistant compound is a polymer, the protein repelling or shielding effect is believed to primarily be due to entropy effects, non-specific protein binding giving rise to an unfavourable entropy increase. The "protein resistant compound" may optionally be a mixture of different protein resistant compounds.

For the sake of simplicity, the term "polymer" is used herein to include oligomers (usually defined as <100 monomer units, especially <30 monomer units) as well as higher molecular polymers.

The most common example of a protein resistant compound is poly(ethylene glycol) (PEG), which is a linear, flexible, hydrophilic and water-soluble polyether, which may have a molecular weight ranging from about 150 to about $10^7$, as well as derivatives and analogues thereof. Usually, the PEG has been derivatized to contain termini that bind to the hydrogel, such as, e.g., with an amine or thiol group. PEG analogues include, for example, PEG-like polymers where the ether linkages are replaced by amide-bonds making the polymer more stable. Other examples of protein resistant compound include dendritic polyglycerol (PG) derivatives (Siegers, C., et al. *Chem. Eur. J.* 2004, 10, 2831-2838), and the protein resistant compounds described by Chapman, R. G., et al., *J. Am. Chem. Soc.* 2000, 122 8303-8304, such as, e.g., $HN(CH_3)CH_2CON(CH_3)_2$. Numerous other protein resistant compounds that may be contemplated for use in the present invention are known to a person skilled in the art.

Coupling of the protein resistant compound and binding agents to the hydrogel is effected through binding elements of the hydrogel and of the protein resistant compound and the binding agent(s), respectively. The binding elements are preferably functional groups to permit the formation of covalent bonds. The functional groups on the hydrogel to which the binding agents are coupled are preferably, but not necessarily of the same kind as the functional groups to which the protein resistant compound is coupled. Exemplary functional groups include hydroxyl, carboxyl, amino, aldehyde, carbonyl, epoxy, vinyl and thiol.

In order to increase the coupling of binding agent, the protein resistant compound may contain an additional functional group(s), which after coupling of the protein resistant compound to the hydrogel is accessible for coupling of binding agent. Many times it may, however, be preferred that the protein resistant compound does not contain such additional functional groups, so that the binding agent is only coupled via the functional groups of the hydrogel.

Usually, functional groups of the hydrogel are activated by an activating agent prior to coupling to the protein resistant compound and the binding agents. Alternatively, functional groups of the protein resistant compound and/or the binding agents may be activated. Methods for activating functional groups are readily apparent to the skilled person and may be selected from a wide variety of methods. Exemplary activated functional groups include for example, reactive ester, hydrazide, thiol, maleimide and a reactive disulphide-containing derivative. Optionally, the activation/coupling of protein resistant compound and/or binding agents may be repeated one or more times. Also the actual coupling steps may optionally be repeated.

When activating the functional groups on the surface, it is often preferred not to activate all the functional groups but only a selected fraction thereof. This is, e.g., the case when the hydrogel is a carboxymethyl-modified dextran where, as is known per se in the art, the residual carboxyl groups will exhibit a negative charge which assists in attracting a positively charged binding agent (and ultimately analyte to the surface). Depending on the type of binding agent, a positive charge thereof may be obtained by selection of the pH.

In a preferred embodiment, the protein resistant compound is bound only to a selected fraction of the activated functional groups, and the binding agent is then bound to remaining activated groups, optionally after repeated activation of functional groups on the surface.

The hydrogel, which may be natural or synthetic, is preferably a polysaccharide, such as, e.g., dextran, cellulose, agarose, carrageenan, alginic acid, starch or derivatives thereof. Preferably, the polysaccharide is dextran or cellulose or a derivative thereof, such as, e.g., carboxymethylated dextran.

The thickness of the hydrogel layer may vary within wide limits, but is usually in the range of from about 30 Å to about 10,000 Å, especially from about 30 Å to about 1,000 Å.

Coupling to the hydrogel may also be effected via other binding elements (coupling groups), such as, e.g., members of specific binding pairs, one member of a specific binding pair being conjugated to the hydrogel and the other to the protein resistant compound and to the binding agent, respectively. For example, the hydrogel may support avidin or streptavidin, and the protein resistant compound and the binding agent may be biotinylated. Alternatively, the hydrogel may support an oligonucleotide and a complementary oligonucleotide may be conjugated to the protein resistant compound and the binding agent, respectively. Optionally, one oligonucleotide duplex may be used for the coupling of the protein resistant compound and a different oligonucleotide duplex for the binding agent.

The binding agent is usually a ligand, which is capable of recognizing a particular analyte in solution. However, the binding agent may also be a capture agent capable of binding a ligand or, optionally, a second capture agent, which in turn binds a ligand.

Examples of ligands include, without any limitation thereto, agonists and antagonists for cell membranes, toxins and venoms, viral epitopes, antigenic determinants, hormones and hormone receptors, steroids, peptides, enzymes, substrates, cofactors, drugs, lectins, sugars, oligonucleotides, oligosaccharides, proteins, glycoproteins, cells, cellular membranes, organelles, cellular receptors, vitamins, viral epitopes, and immunoglobulins, e.g., monoclonal and polyclonal antibodies. Among ligands of particular interest may be mentioned those mediating a biological function on binding with a particular analyte(s).

Analytes that may be assayed for include, without any restriction thereto, agonists and antagonists for cell membrane receptors, toxins and venoms, viral epitopes, hormones (e.g., opiates, steroids, etc), hormone receptors, peptides, enzymes, enzyme substrates, cofactors, drugs, lectins, sugars, oligonucleotides, oligosaccharides, proteins, monoclonal and polyclonal antibodies, and small molecules.

The solid support is preferably a rigid structure and may comprise a substrate having a surface layer of a different material. Exemplary substrate materials are polymers, such as (poly)tetrafluoroethylene, (poly)vinylidenedifluoride, or combinations thereof. A preferred substrate material for many applications is flat glass. The top layer of the solid support may be of another material than the rest of the solid support. A suitable surface for many applications is a metal film, e.g., gold, silver or aluminum, preferably gold.

With the procedure of the invention, it is possible to prepare a reactive solid support surface which, despite having a relatively high level of immobilized protein resistant compound, still has a high level of an immobilized binding agent, such as a ligand. In many situations, it is preferred that the amount of protein resistant compound bound to the surface is not less than about 2 ng/mm$^2$. Likewise it is often preferred that the amount of immobilized binding agent (ligand) is not less than about 9 ng/mm$^2$.

While a reactive solid support surface prepared as described above may be used for any purpose where it is desired to bind one or more species to the binding agent(s) while substantially reducing or preventing non-specific binding, the support surface is preferably used for analytical purposes, e.g., in assays for qualitative or quantitative analyte determination. Such a surface is herein sometimes referred to as a "sensing surface".

When performing an assay for an analyte in a sample, the binding agent bound to the surface may be an analyte-specific ligand, the analyte or an analyte analogue, or a capture agent which in turn binds an analyte-specific ligand. A variety of assay formats well-known to the skilled person may be used, the three assay types briefly described below (with respect to mass sensing-based detection) being only exemplary.

In an inhibition type assay, the analyte or an analyte analogue is immobilized on the sensing surface. A high molecular weight detecting molecule, such as an antibody, is added to the sample, and the detecting molecules (in excess concentration) bind to the analyte. When the sample is passed over the sensing surface, remaining free detecting molecules in the sample will bind to the surface, and the detected response is inversely related to the amount of analyte in the sample.

In a competition type assay, the analyte or an analyte analogue is conjugated to a high molecular weight carrier forming a high molecular weight complex which is added to the sample to compete with the analyte for the binding to analyte-specific ligand (e.g., an antibody) immobilized on the sensing surface. The detected response, which will be almost entirely attributable to the high molecular weight carrier, is inversely related to the analyte concentration in the sample.

In a sandwich assay, the response obtained when analyte binds to analyte-specific ligand immobilized on the sensing surface is enhanced by passing over the surface a secondary reagent which binds specifically to bound analyte. The enhancement may be due to the secondary or "sandwich" reagent being either a larger molecule or (less commonly) a molecule that binds in a many-to-one ratio. The detected response is directly related to the analyte concentration in the sample.

The reactive solid support surface may also be used for studying analyte/ligand interactions at the surface for determining kinetic parameters for the interaction, such as association and dissociation rate constants and affinity.

The reactive solid support surface with immobilized protein resistant compound and binding agents may also be in the form of an array, where discrete areas or "spots" support different or the same binding agents. Optionally, the hydrogel coating is also in array form, i.e., the coating layer consists of separate hydrogel patches.

To benefit from the non-specific binding-resisting surface of the present invention, the sample is usually based on a "complex" medium containing non-analyte species which may bind non-specifically to the surface.

Such a complex medium upon which the sample is based may be selected from numerous such media containing one or more analytes of interest. Exemplary complex media include body fluids, such as cerebrospinal fluid, saliva, breast milk, urine, bile, whole blood, blood serum or plasma, tears, homogenized biopsies, as well as other complex media such as cell culture media, cell lysates, crude plant extracts, extracted or dissolved food stuffs, liquid food stuffs, such as beverages (milk, fruit juices, beer etc).

Depending on the particular complex medium to be analyzed, the tested sample may be the original sample as taken or a dilution thereof with a suitable diluent. Generally, the complex medium content of the sample may range from about 1 to about 100% (v/v), usually from about 10 to about 100% (v/v), especially from about 30 to about 100% (v/v), for example from about 30 to about 50% (v/v).

A particular assay for which the reactive solid support surface prepared according to the invention may be used is for immunogenicity studies, immunogenicity being the ability of a substance to induce an immune response, especially in a mammal, such as a human being. These studies are usually performed on blood sera to analyze antibodies therein. Such antibodies may, e.g., be produced in response to certain drugs, such as protein drugs, and may give rise to undesired side-effects in the patient which reduce the efficacy of the drug, shorten the time that the drug remains in the body, and may lead to allergic reactions. The antibodies elicited against the drug may also cross-react with autologous antibodies and cause severe problems. The use of an SPR-biosensor with a sensor surface having an attached carboxymethyl-modified dextran hydrogel for determination if an immune response against a therapeutic agent has occurred is, for example, described in US 2003/0040027 A1 (the disclosure of which is incorporated by reference herein).

It is often also of interest to analyze antibodies in blood sera produced in response to vaccination to determine the success of the vaccination.

While, as mentioned above, problems with non-specific binding may be especially severe with mass-sensing sensors, analyses and assays performed with the reactive solid support surfaces prepared according to the present invention may be used with numerous detecting principles including those relying on the detection of a label, such as a radiolabel, a chromophore, a fluorophore, etc, as well as label-free techniques. In many cases, real time detection systems are preferred, especially those based on chemical sensor or biosensor technology.

A biosensor is broadly defined as a device that uses a component for molecular recognition (for example a layer with immobilized antibodies) in either direct conjunction with a solid state physicochemical transducer, or with a mobile carrier bead/particle being in conjunction with the transducer. While such sensors are typically based on label-free techniques detecting a change in mass, refractive index or thickness for the immobilized layer, there are also biosensors relying on some kind of labelling. Typical sensors for the purposes of the present invention include, but are not limited to, mass detection methods, such as optical methods and piezoelectric or acoustic wave methods, including, e.g., surface acoustic wave (SAW) and quartz crystal microbalance (QCM) methods. Representative optical detection methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors, external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Biosensor systems based on SPR and other detection techniques are commercially available today. Exemplary such SPR-biosensors include the above-mentioned BIACORE® instruments. A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instrument may be found in U.S. Pat. No. 5,492,840. The full disclosures of the above-mentioned U.S. patents are incorporated by reference herein.

A sensor chip frequently used in the BIACORE® instruments has a gold-coated surface with a covalently linked carboxymethyl-modified dextran polymer hydrogel. The protein resistant compound, such as poly(ethylene glycol) (PEG) chains with binding termini, and binding agents, below referred to as "ligands", may be covalently coupled to such a sensor chip in several ways.

In "amine coupling", carboxyl groups of the modified dextran matrix are activated by 1-ethyl-3-(3-dimethylaminopropyl)-carbodiimide (EDC) and N-hydroxysuccinimide (NHS) to give reactive succinimide esters, which then react spontaneously with amine and other nucleophilic groups, allowing direct immobilization of ligands containing such groups. Other groups can be introduced onto the dextran matrix once it has been activated with EDC/NHS. One example is the introduction of reactive disulfides that can be used in a thiol-disulfide exchange reaction to immobilize thiol-containing ligands. Another example is the introduction of hydrazide groups which can react with cis-diols obtained by aldehyde-containing molecules.

"Thiol-coupling" utilizes exchange reactions between thiols and active disulfide groups. The active disulfide may be introduced either on the dextran matrix to exchange with a thiol group on the ligand (ligand thiol approach), or on the ligand molecule to exchange with a thiol group introduced on the dextran matrix (surface thiol approach). A common reagent for introducing active disulfide groups is 2-(2-pyridinylthio)-ethaneamine (PDEA). An alternative approach is reaction of thiol groups on the ligand with maleimide reagents introduced on the dextran matrix.

In "aldehyde coupling", ligands containing aldehyde groups (either native or introduced by oxidation of cis-diols, e.g., using sodium metaperiodate) can be immobilized after activating the surface with hydrazine or carbohydrazide.

In the following Example, various aspects of the present invention are disclosed more specifically for purposes of illustration and not limitation.

EXAMPLE

Instrumentation

A BIACORE® 3000 (Biacore AB, Uppsala, Sweden) was used. This instrument, which is based on surface plasmon resonance (SPR) detection at a gold surface, uses a microfluidic system for passing samples and running buffer through four individually detected flow cells, designated Fc1 to Fc4, one by one or in series. As sensor chip was used Series CM5 (Biacore AB, Uppsala, Sweden) which has a gold-coated (about 50 nm) surface with a covalently linked hydrogel matrix (about 100 nm) of carboxymethyl-modified dextran polymer. As running buffer was used HBS-EP (Biacore AB). Unless indicated otherwise, the flow rate was 5 µl/min. The output from the instrument is a "sensorgram" which is a plot of detector response (measured in "resonance units", RU) as a function of time. An increase of 1000 RU corresponds to an increase of mass on the sensor surface of approximately 1 $ng/mm^2$.

Rat Sera

In the experiments below were used sera from rats (Wistar F) which had and had not, respectively, been vaccinated against allergy to elicit anti-IgE antibodies (Resistentia Pharmaceuticals AB, Uppsala, Sweden). The vaccine was a histidine-tagged recombinant protein, called his-ORO, containing the receptor-binding domain from rat IgE flanked by the same domain from opossum IgE (Opossum-Rat-Opossum). The rats were vaccinated three times with 20 or 100 µg of his-ORO. Control rats were injected with PBS (phosphate buffered saline) instead of vaccine.

Optimization of Ligand (IgE) Concentration

A CM5 sensor chip was activated for 7 minutes with 0.4 M aqueous 1-ethyl-3-(3-dimethylaminopropyl)-carbodiimide (EDC) and 0.1 M aqueous N-hydroxysuccinimide (NHS). Different concentrations of rat IgE (Zymed Laboratories, Inc., South San Fransisco, Calif., U.S.A.) in 10 mM Na-acetate, pH 5.5, were then injected into flow cells Fc1 to Fc4 of the BIACORE® 3000. The chip surface was then deactivated for 7 min with 1 M ethanolamine-HCl, pH 8.5. The activity of the surface was verified by injection of mouse anti-rat IgE (MARE) monoclonal antibody (Serotec Ltd., Kidlington, U.K.) (analyte) at 20 µg/ml. Regeneration of the surface was performed with 10 mM glycine, pH 2.0. The results are shown in Table I below.

TABLE I

| Flow cell | Rat IgE conc. µg/ml | Immobilized (RU) | Analyte response (RU) |
|---|---|---|---|
| Fc1 | 5 | 8829 | 2525 |
| Fc2 | 10 | 15271 | 2827 |
| Fc3 | 20 | 16504 | 2680 |
| Fc4 | 30 | 16539 | 2582 |

From the table it is seen that a plateau is reached at about 10 µg/ml of rat IgE which would provide robust coupling conditions, and this concentration was therefore selected for the experiments below. The level of immobilized IgE to be used was, however, selected to be about 9000 RU.

Immobilization of PEG and IgE

Activation of a CM5 sensor chip with EDC/NHS in flow cells Fc1 to Fc3 was performed for 7 min as described above. 5 mM methoxy-poly(ethylene glycol) amine (methoxy-PEG-amine; $CH_3O$—$(CH_2CH_2O)_n$—$CH_2CH_2$—$NH_2$), MW 5000 Da (Shearwater Polymers, Inc., Huntsville, Ala., U.S.A.) in borate buffer (10 mM Na-borate, 1 M NaCl, pH 8.5) were then injected through flow cells Fc1 and Fc2 for 7 min. To increase the amount of immobilized PEG in Fc2, the activation was repeated and 10 mM methoxy-PEG-amine were injected for 7 min. The sensor chip was then left over-night at stand-by flow, after which the surface was activated again followed by injection of 10 µg/ml of rat IgE (Zymed Laboratories, Inc.) in 10 mM Na-acetate, pH 4.5, through Fc1 to Fc3. The "Aim for ligand level" wizard of the instrument control software was used to obtain an IgE immobilization level of about 9000 RU. Deactivation was then performed for 7 min with 1 M ethanolamine-HCl, pH 8.5.

The immobilization levels of PEG and IgE obtained in flow cells Fc1 to Fc3 were as follows:

Fc1: 1107 RU PEG, 9557 RU IgE
Fc2: 2301 RU PEG, 8265 RU IgE
Fc3: 8150 RU IgE.

Analysis of Rat Sera

Figure 2:
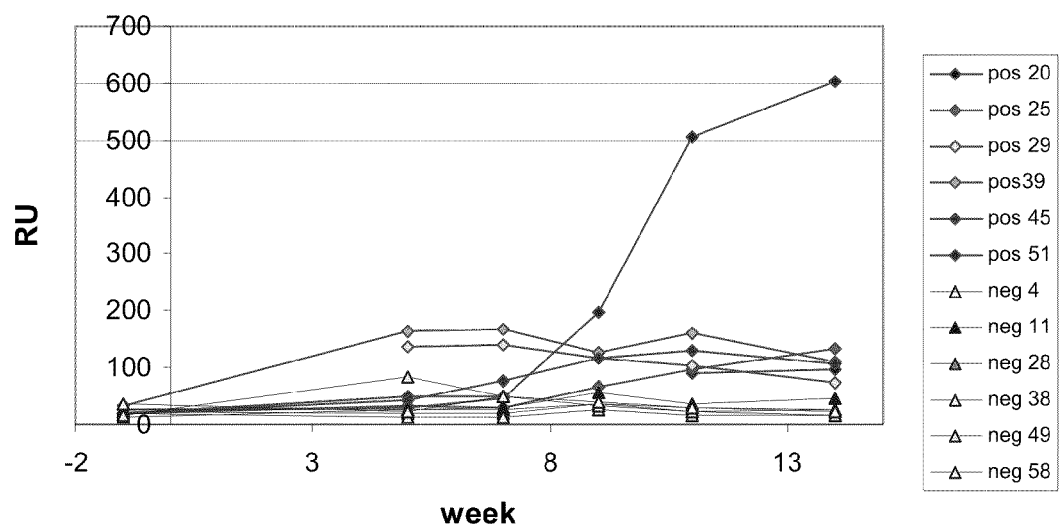
FIG. 2 is a diagram showing rat serum anti-IgE responses versus time after immunization for vaccinated and control animals, respectively, on a sensor surface with immobilized IgE and methoxy poly(ethylene glycol) amine at a first surface concentration thereof.
Figure 3:
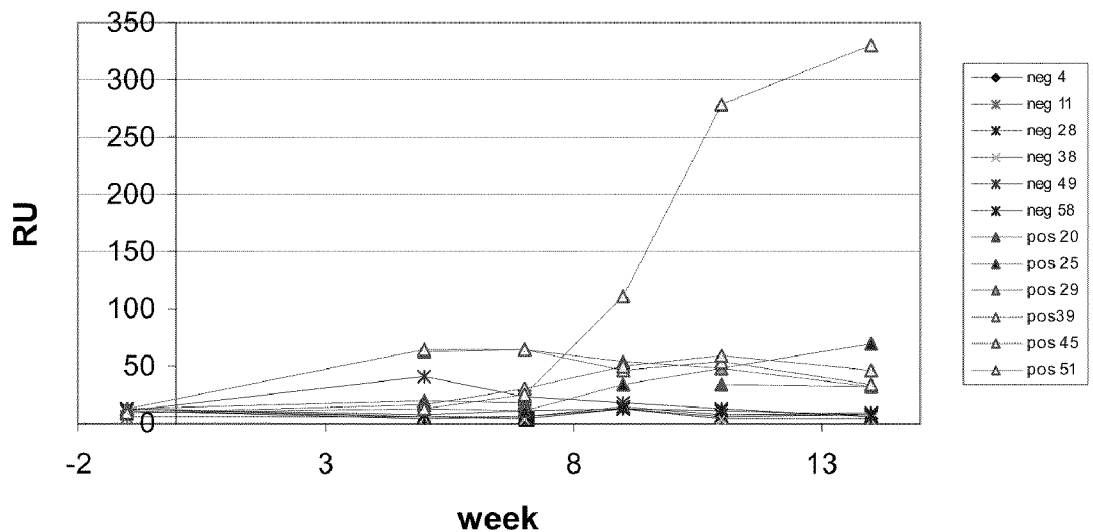
FIG. 3 is a diagram showing rat serum anti-IgE responses versus time after immunization for vaccinated and control animals, respectively, on a sensor surface with immobilized IgE and methoxy poly(ethylene glycol) amine at a second surface concentration thereof.

Six negative rat sera (serum nos. 4, 11, 28, 38, 49, 58) and six positive rat sera (serum nos. 20, 25, 39, 45, 51) were taken at week −1, 5, 7, 9, 11 and 14 after vaccination of the animals (week −1 being 1 week before vaccination). The sera were diluted 5 times in HBS-EP (Biacore AB) and analyzed using the CM5 chip immobilized with PEG and IgE as obtained above. The sera were injected serially through the flow cells using the "kinject" command, and the respective responses were determined. 20 µg/ml of MARE (Serotec Ltd.) was used as control. Regeneration of the surface between each serum injection was performed with 10 mM glycine, pH 2.25, for 1 minute and 10 mM NaOH for 30 seconds. The "extraclean" command was used after each regeneration. The results are shown in FIGS. 1 to 3.

The limit of detection (LOD) was calculated as:

$$AVERAGE_{negative\ samples} + 3*SD_{negative\ samples}$$
(SD=standard deviation)

Samples having responses higher than LOD are therefore positive with a probability of 99.9%. To conveniently determine which samples can be detected as positive, the response (in RU) is divided by LOD. A ratio higher than 1 thereby indicates a positive sample.

The responses for the vaccinated animals were divided by LOD calculated for all 6 unvaccinated animals at all six times, and the results are presented in Tables II to IV below. Samples that can be detected as positive are marked in bold type. (Two samples were missing, animal 29 week −1 and animal 20 week 9)

TABLE II

8150 RU IgE RESPONSE/LOD

| Week | Serum 20 | Serum 25 | Serum 29 | Serum 39 | Serum 45 | Serum 51 |
|---|---|---|---|---|---|---|
| −1 | 0.14 | 0.22 | | 0.18 | 0.13 | 0.32 |
| 5 | 0.49 | 0.66 | 0.78 | 0.96 | 0.58 | 0.32 |
| 7 | 0.51 | 0.43 | 0.81 | 1.00 | 1.15 | 0.34 |
| 9 | | 0.64 | 0.73 | 0.80 | 1.20 | 0.96 |
| 11 | 0.88 | 0.81 | 0.79 | 1.07 | 1.24 | 2.32 |
| 14 | 1.02 | 1.00 | 0.62 | 0.76 | 1.05 | 2.65 |

TABLE III

1107 RU PEG + 9557 RU IgE RESPONSE/LOD

| Week | Serum 20 | Serum 25 | Serum 29 | Serum 39 | Serum 45 | Serum 51 |
|---|---|---|---|---|---|---|
| −1 | 0.28 | 0.28 | | 0.47 | 0.28 | 0.38 |
| 5 | 0.68 | 0.47 | 1.91 | 2.29 | 0.61 | 0.43 |
| 7 | 0.69 | 0.41 | 1.95 | 2.33 | 1.07 | 0.66 |
| 9 | | 0.94 | 1.61 | 1.76 | 1.63 | 2.71 |
| 11 | 1.26 | 1.34 | 1.46 | 2.22 | 1.81 | 7.02 |
| 14 | 1.37 | 1.85 | 1.01 | 1.54 | 1.49 | 8.33 |

TABLE IV

2301 RU PEG + 8265 RU IgE RESPONSE/LOD

| Week | Serum 20 | Serum 25 | Serum 29 | Serum 39 | Serum 45 | Serum 51 |
|---|---|---|---|---|---|---|
| −1 | 0.39 | 0.31 | | 0.40 | 0.32 | 0.29 |
| 5 | 0.62 | 0.44 | 2.05 | 2.13 | 0.51 | 0.41 |
| 7 | 0.61 | 0.38 | 2.10 | 2.10 | 1.02 | 0.79 |
| 9 | | 1.10 | 1.77 | 1.52 | 1.64 | 3.62 |
| 11 | 1.08 | 1.60 | 1.58 | 1.74 | 1.94 | 9.15 |
| 14 | 1.04 | 2.30 | 1.06 | 1.10 | 1.51 | 10.83 |

As can be seen from FIGS. 1 to 3, 9-14 weeks from vaccination, sera from vaccinated animals had anti-IgE responses of 249 to 1032 RU on an "IgE surface", and sera from control animals had 97-385 RU, i.e., a poor separation between vaccinated and control animals. The corresponding samples on the "2301 RU PEG+8265 RU IgE" surface gave 32-330 RU for vaccinated animals and 8-13 RU for controls. The high PEG level (2301 RU) is better than the lower one (1107 RU). As is shown in Tables II to IV, only 10 of 29 potentially positive samples are detected without PEG, whereas 22 of 29 samples are detected as positive with the high PEG level.

Optimization of the Amount of PEG

Figure 4:
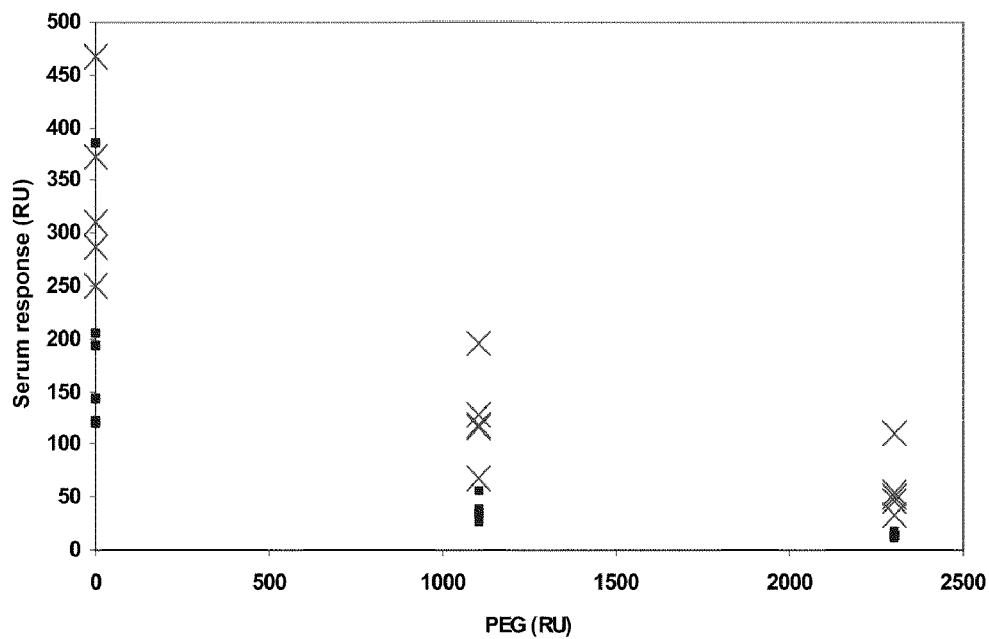
FIG. 4 is a diagram showing rat serum anti-IgE responses on sensor surfaces with immobilized IgE and different surface concentrations of methoxy poly(ethylene glycol) amine.

The results at week 9 for (vaccinated) serum nos. 25, 29, 39, 45 and 51 from Tables I to IV above are put together in FIG. 4 and in Table V below. In FIG. 4, "X" designates a positive serum and "■" designates a negative serum.

TABLE V

| Serum (vaccinated) | 0 RU PEG response/LOD | 1107 RU PEG response/LOD | 2301 RU PEG response/LOD |
|---|---|---|---|
| Serum 25 | 0.64 | 0.94 | 1.10 |
| Serum 29 | 0.73 | 1.61 | 1.77 |
| Serum 39 | 0.80 | 1.76 | 1.52 |
| Serum 45 | 1.20 | 1.63 | 1.64 |
| Serum 51 | 0.96 | 2.71 | 3.62 |

From Table V and FIG. 4, it is clearly seen that more samples can be detected as positive, the more PEG there is on the surface, despite the fact that the response levels for the positive samples have been considerably reduced.

It is to be understood that the invention is not limited to the particular embodiments of the invention described above, but the scope of the invention will be established by the appended claims.

The invention claimed is:

1. A method of preparing a reactive solid support surface for surface sensitive detection, which method comprises the steps of:

a) providing a solid support having a hydrogel coating with a plurality of binding elements, and activating said binding elements to a state capable of forming covalent bonds;
b) coupling a protein resistant compound to the hydrogel via a first fraction of the activated binding elements;
c) re-activating remaining unreacted binding elements on said hydrogel to a state capable of forming covalent bonds; and then
d) coupling at least one binding agent to the hydrogel via a second fraction of the binding elements, wherein the second fraction of the binding elements comprise those remaining on the hydrogel after coupling of the protein resistant compound via the first fraction of the binding elements;

such that the protein resistant compound and the at least one binding agent are co-immobilized to the hydrogel via the first and second fractions of the binding elements, respectively and intermixed laterally thereon, and wherein said surface sensitive detection is a biosensor system based on mass sensing.

2. The method according to claim 1, wherein the binding elements of the hydrogel comprise functional groups, and the protein resistant compound and the at least one binding agent are covalently coupled to the hydrogel via the functional groups.

3. The method according to claim 2, wherein the protein resistant compound and the at least one binding agent are coupled to the same kind of functional group of the hydrogel.

4. The method according to claim 1, wherein the activated functional groups are selected from reactive ester, hydrazide, thiol, maleimide and reactive disulphide-containing derivative.

5. The method according to claim 2, wherein the protein resistant compound and the binding agent each contain a functional group independently selected from amine, thiol and a reactive disulphide-containing derivative.

6. The method according to claim 1, wherein the binding elements of the hydrogel comprise one member of a specific binding pair and the protein resistant compound and the at least one binding agent contain the other member of the specific binding pair.

7. The method according to claim 1, wherein the protein resistant compound is a hydrophilic polymer.

8. The method according to claim 1, wherein the protein resistant compound comprises poly(ethylene glycol) or a derivative thereof.

9. The method according to claim 1, wherein the hydrogel is a polysaccharide.

10. The method according to claim 9, wherein the polysaccharide is selected from agarose, dextran, carrageenan, alginic acid, starch, cellulose, and derivatives thereof.

11. The method according to claim 9, wherein the polysaccharide is dextran or a derivative thereof.

12. The method according to claim 9, wherein the polysaccharide is cellulose or a derivative thereof.

13. The method according to claim 1, wherein the binding agent is a ligand capable of specifically binding to an analyte.

14. The method according to claim 1, wherein the binding agent is a capture agent capable of binding to an analyte-specific ligand.

15. The method according to claim 1, wherein the amount of protein resistant compound that is coupled in step b) of claim 1 is not less than about 2 ng/mm$^2$.

16. The method according to claim 1, wherein the amount of binding agent that is coupled in step c) of claim 1 is not less than about 9 ng/mm$^2$.

17. The method according to claim 1, wherein the solid support surface to which the hydrogel is attached comprises a metal layer.

18. The method according to claim 17, wherein the hydrogel is attached to the metal layer via an ordered monolayer of alkyl chains.

19. The method according to claim 1, wherein the hydrogel coating on the solid support comprises an array of defined discrete areas.

20. The method according to claim 1, wherein the mass sensing biosensor system is based on surface plasmon resonance.

* * * * *